United States Patent
Lee

[11] Patent Number: 5,947,943
[45] Date of Patent: Sep. 7, 1999

[54] DIAPER VISUAL INDICATOR

[76] Inventor: Frances Meiling Lee, 1864 Skyline Dr., Honolulu, Hi. 96817

[21] Appl. No.: 09/017,273

[22] Filed: Feb. 2, 1998

[51] Int. Cl.⁶ .................................................... A61F 13/15
[52] U.S. Cl. ............................................................ 604/361
[58] Field of Search ............................................ 604/361

[56] References Cited

U.S. PATENT DOCUMENTS

| | | | |
|---|---|---|---|
| 3,759,261 | 9/1973 | Wang | 604/361 |
| 3,952,746 | 4/1976 | Summers | 604/361 |
| 4,738,674 | 4/1988 | Todd et al. | 604/361 |
| 4,834,733 | 5/1989 | Huntoon et al. | 604/361 |
| 4,931,051 | 6/1990 | Castello | 604/361 |
| 5,291,181 | 3/1994 | DePonte . | |
| 5,395,385 | 3/1995 | Lu . | |
| 5,537,095 | 7/1996 | Dick et al. . | |
| 5,570,082 | 10/1996 | Mahgerefteh . | |

FOREIGN PATENT DOCUMENTS

| | | | |
|---|---|---|---|
| 2541872 | 9/1984 | France | 604/361 |

Primary Examiner—Mark O. Polutta
Attorney, Agent, or Firm—Michael I. Kroll

[57] ABSTRACT

The present invention relates to an absorbent article (10) of the type having a liquid-permeable top sheet (14), a liquid-impermeable back sheet (16) having an exterior-facing side (20) and an interior-facing side (22), and an absorbent core (18) disposed between the top sheet (14) and the back sheet (16), further including a wetness-indicating material (24) disposed on the interior-facing side (22) of the back sheet (16) which changes appearance after exposure to moisture (26). The exterior-facing side (20) of the back sheet (16) generally has a light appearance when dry and the wetness-indicating material (24) has a light appearance when dry and a dark appearance when wet. The back sheet (16) can include a translucent moisture barrier layer (28) on the exterior facing side (20) and a liquid-permeable layer (30) on the interior side (22), with the wetness-indicating material (24) between the moisture barrier layer (28) and the liquid-permeable layer (30).

1 Claim, 3 Drawing Sheets

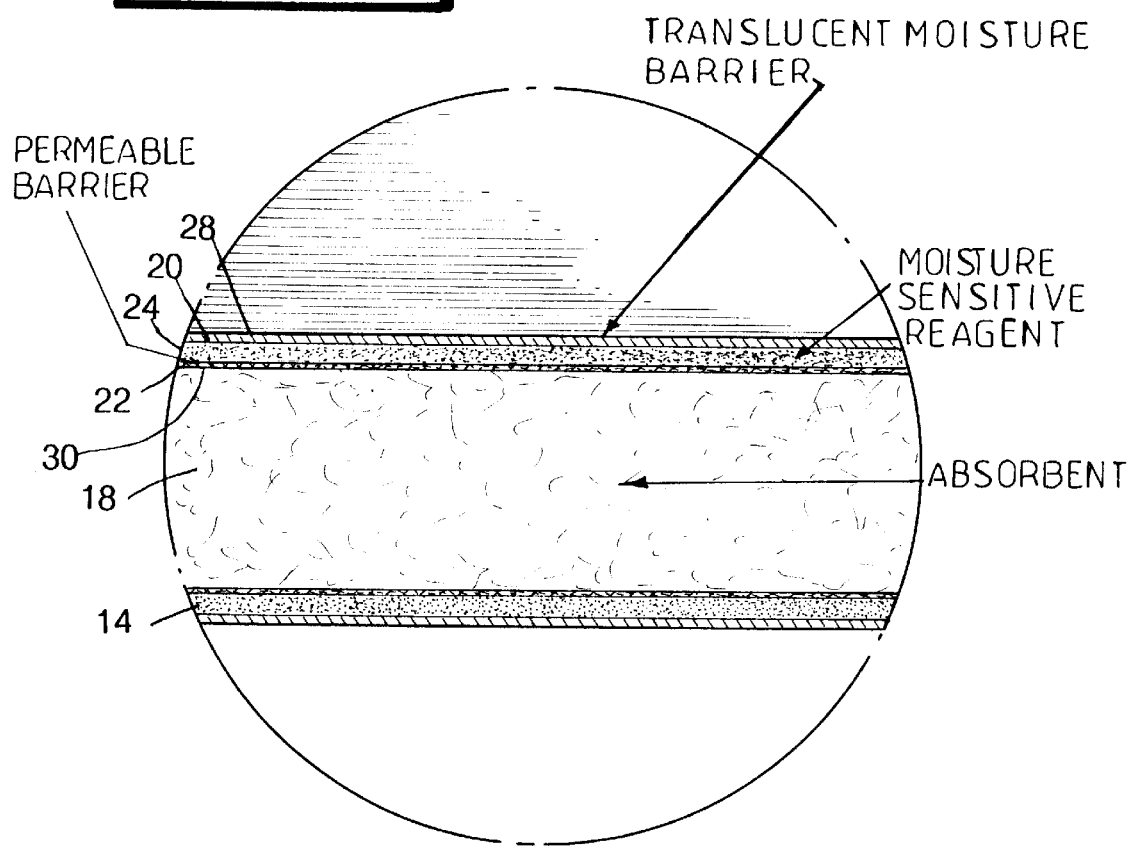
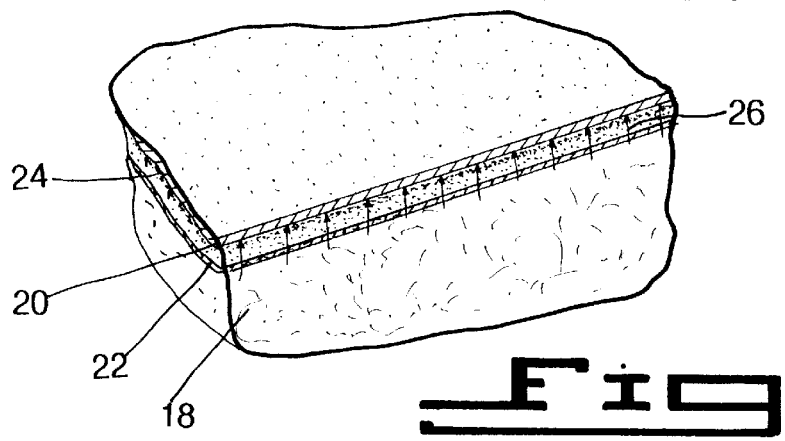

DIAPER VISUAL INDICATOR

BACKGROUND OF THE INVENTION

1. Field of the Invention

The instant invention relates generally to absorbent articles and more specifically to diapers or other articles for incontinence having a visually perceptible wetness indicator.

2. Description of the Prior Art

Wetness indicators for diapers and/or incontinence pads are known in the art. For example, U.S. Pat. No. 5,291,181 (DePonte, D. A., et al., Mar. 1, 1994) discloses a monitoring system for detecting the presence of urine on a pad. The system relies on an electric circuit which is completed in the presence of urine.

U.S. Pat. No. 5,395,358 (Lu, C. B., Mar. 7, 1995) discloses a wetness indicator for a diaper which comprises a battery-powered mechanism which is inserted into the diaper and which, when placed in contact with an electrolyte-containing liquid (such as urine), forms a complete circuit and emits an audible signal indicating the diaper requires changing.

U.S. Pat. No. 5,537,095 (Dick, B. R., et al., Jul. 16, 1996) discloses an incontinence detection device comprising a pad and a plurality of circuits spaced on the pad. A controller applies voltage from a power source in order to determine that an incontinent event has occurred at a certain minimum liquid volume.

U.S. Pat. No. 5,570,082 (Mahgerefteh, N., et al., Oct. 29, 1996) discloses an incontinence detection device comprising a pad and a plurality of circuits spaced on the pad. A controller applies voltage from a power source in order to determine that an incontinent event has occurred at a certain minimum liquid volume.

BRIEF SUMMARY OF THE INVENTION

The present invention is concerned with absorbent articles such as diapers, adult incontinent briefs and the like, and more particularly, the present invention relates to absorbent articles having a readily discernible indication of use.

A primary object of the present invention is to provide an absorbent article having a liquid-permeable top sheet, a liquid-impermeable back sheet, and an absorbent core between the top and back sheets, and a wetness-indicating material on the inside of the back sheet which changes appearance after exposure to moisture.

Another object of the present invention is to provide an absorbent article having a liquid-permeable top sheet, a liquid-impermeable back sheet, an absorbent core disposed between the back and top sheets, and a wetness-indicating material disposed within the absorbent core which changes appearance when wet, or when in contact with any form of moisture.

Another object of the present invention is to provide an absorbent article having a back sheet generally light in appearance when dry and a wetness-indicating material which is light in appearance when dry and dark in appearance when wet.

An additional object of the present invention is to provide an absorbent article having a translucent moisture barrier layer on the exterior facing side and a liquid-permeable layer on the interior side, with the wetness-indicating material between the moisture barrier layer and the liquid-permeable layer.

Another object of the present invention is to provide an absorbent article which can be quickly and easily checked for wetness without the need for touching the article.

A further object of the present invention is to provide an absorbent article which can be quickly and easily checked for wetness simply by making a visual examination of the exterior surface of the article.

Another object of the present invention is to provide an absorbent article having a visual indication of wetness utilizing a color intensity which is directly proportional to the degree of wetness.

Yet another object of the present invention is to provide an absorbent article having a wetness-indicator which is a pH-sensitive cellulosic material.

A further object of the present invention is to provide a disposable or non-disposable, absorbent article that is easy to use, economical to manufacture and safe and convenient to dispose.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 4 is an enlarged cross-sectional view taken from 4 of FIG. 3.

FIG. 5 is a section view of a portion of FIG. 4, illustrating the positive correlation between color intensity and moisture content.

DETAILED DESCRIPTION OF THE PREFERRED EMBODIMENTS

Figure 1:
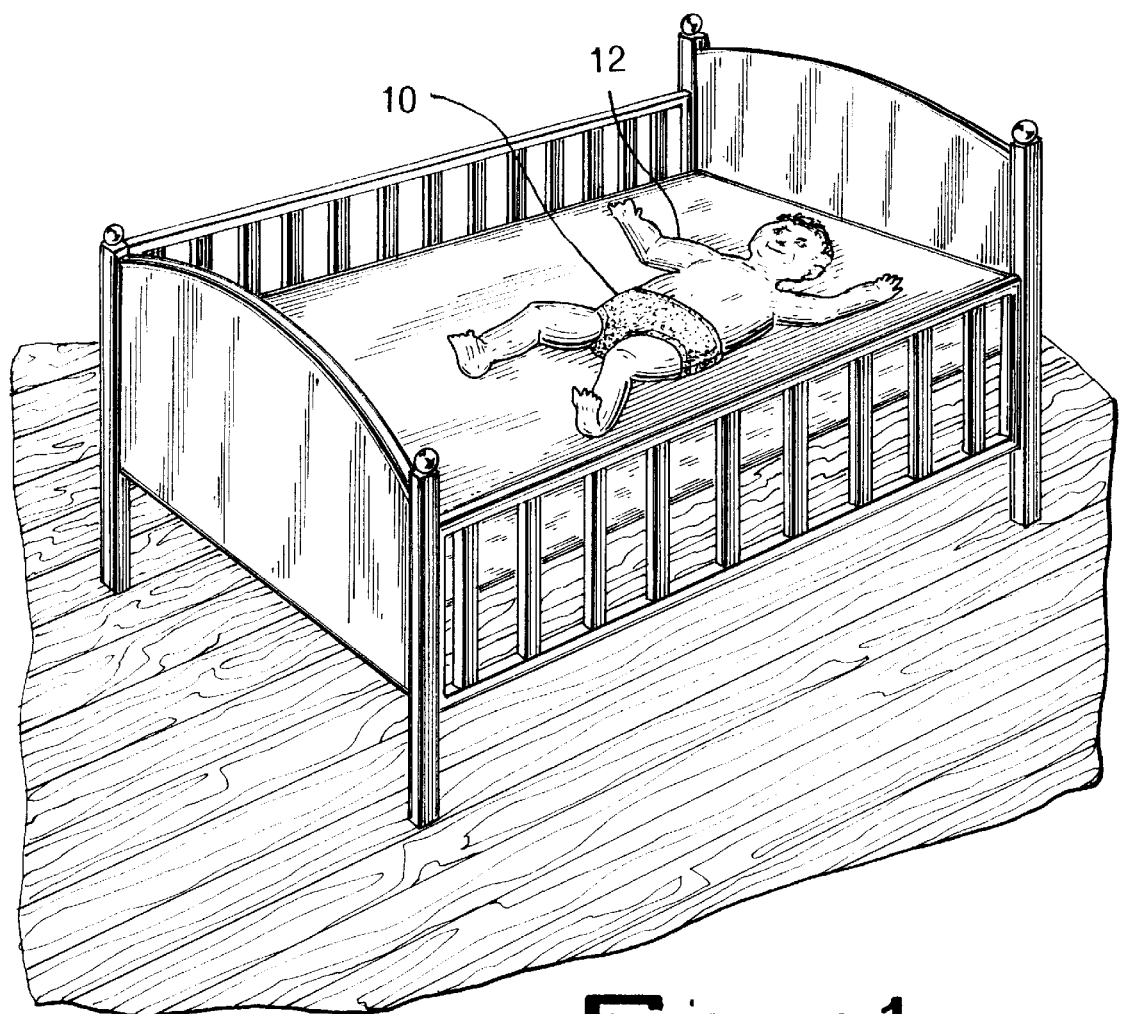
FIG. 1 is a top view of an infant wearing an absorbent article, a diaper, of the present invention.

Turning now descriptively to the drawings, in which similar reference characters denote similar elements throughout the several views, the Figures illustrate an absorbent article of the present invention. With regard to the reference numerals used, the following numbering is used throughout the various drawing figures.

10 absorbent article
12 infant wearing 10
14 top sheet of 10
16 back sheet of 10

18 absorbent core of 10
20 exterior-facing side of 16
22 interior-facing side of 16
24 wetness-indicating material
26 movement of moisture (water) into 24
28 translucent moisture barrier layer on 20
30 liquid-permeable layer on 22

Figure 2:
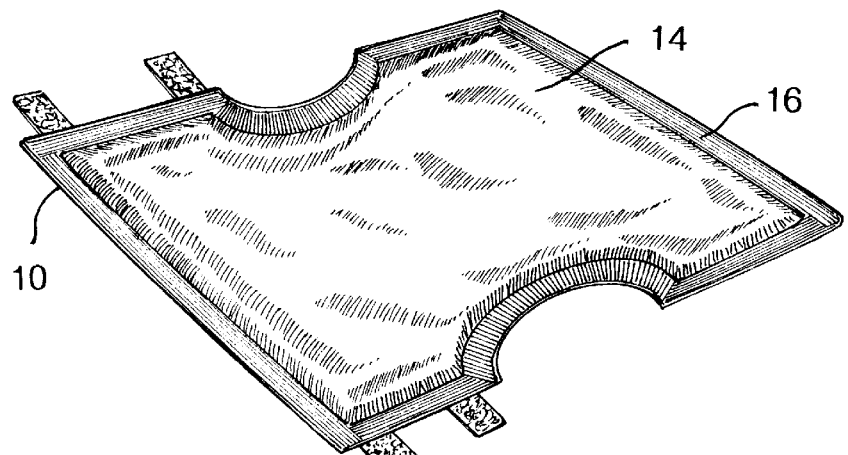
FIG. 2 is an overview of an absorbent article, a diaper, of the present invention.
Figure 3:
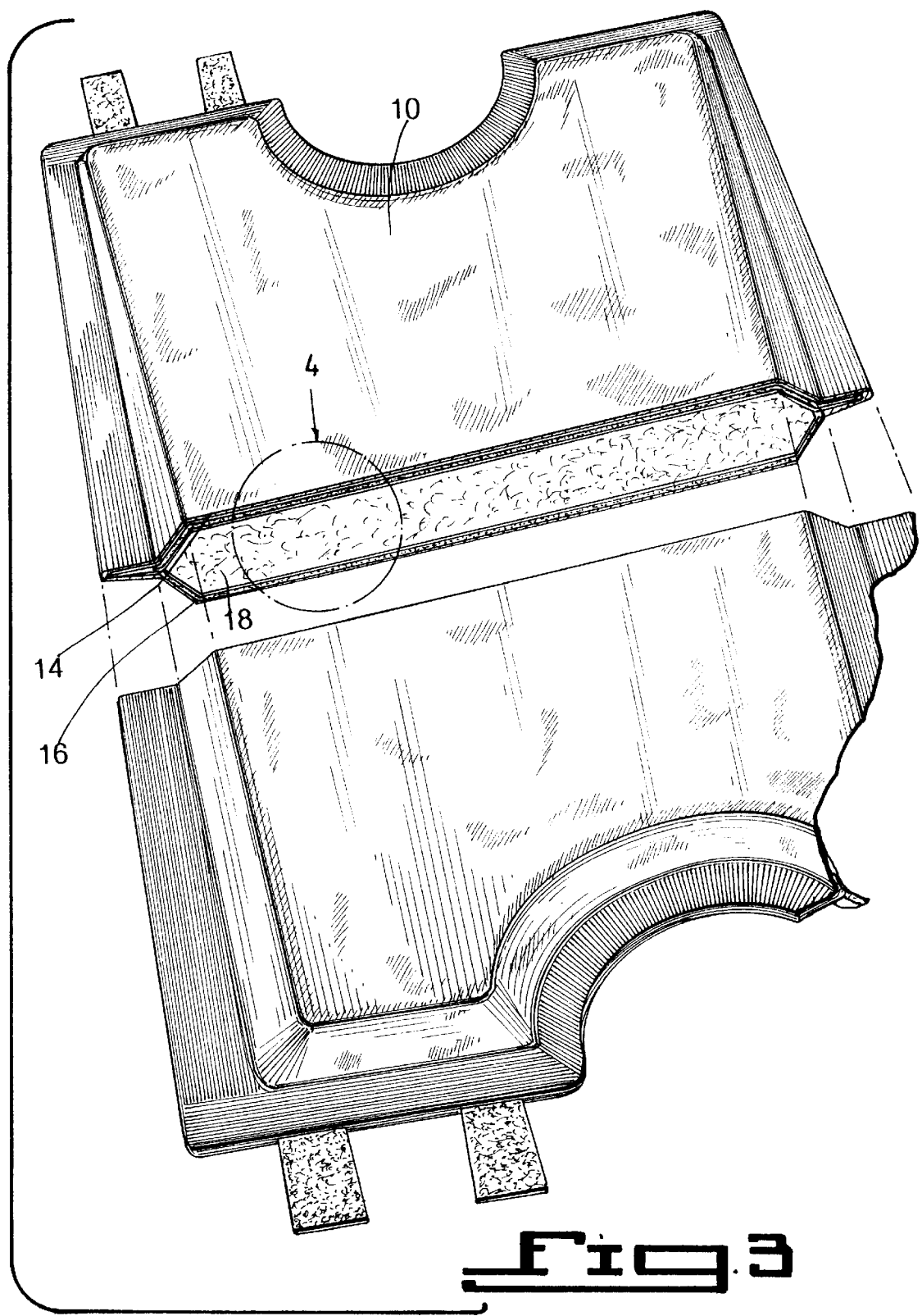
FIG. 3 is a view similar to that in FIG. 2, in cutaway, of a diaper of the present invention showing the various layers in composition.

FIGS. 1 through 5 illustrate an absorbent article 10 comprising a liquid-permeable top sheet 14, a liquid-impermeable back sheet 16 having an exterior-facing side 20 and an interior-facing side 22, an absorbent core 18 disposed between said top sheet 14 and said back sheet 16, and a wetness-indicating material 24 disposed on said interior-facing side 22 of said back sheet 16 which changes appearance after exposure to moisture 26.

Generally speaking, absorbent articles used as diapers or adult incontinence articles have a light appearance, usually white or slightly off-white. In a preferred embodiment of the present invention, the wetness-indicating material 24 turns dark when it becomes wet 26, thereby providing a readily discernible indication that the article is wet and needs to be changed. It is noted that the invention is intended to include all visually perceptible indications of wetness, including changes from one color to another or changes in color intensity. Any color change is included within the scope of the invention, for example, fluorescent, "day-glo," pastel or any other color. In one embodiment of the invention the wetness-indicating material changes color after exposure to moisture, rather than simply changing darker. In another embodiment, the wetness-indicating material is a pH sensitive cellulosic material, for example, litmus paper. Upon exposure to liquid within a desired pH range, the material will change color. The pH range and particular colors are a matter of choice, as the art allows many choices in pH sensitive paper. In another embodiment of the invention, the color change can be seen in stages, becoming more pronounced or different as the article becomes wetter. Additionally, any type of wetness-indicating material can be suitably employed in the practice of the invention.

The absorbent articles of the present invention are suitable for use in any application wherein absorbency and sanitation are desired. For example, the articles of the present invention can be used as diapers, both disposable and reusable, adult incontinence articles, cleaning pads, medical sanitation pads and the like.

With regard to the back sheet 16, it is anticipated that it includes a translucent moisture barrier layer 28 on the exterior facing side 20 and a liquid-permeable layer 30 on the interior side 22, with the wetness-indicating material 24 disposed between the translucent moisture barrier layer 28 and the liquid-permeable layer 30. By "translucent," it is meant that the material is non-opaque, that is, that the moisture barrier 28 is transparent or translucent, so that the visual appearance of the wetness-indicating material 24 can be perceived through the moisture barrier 28. As described previously, the wetness-indicating material will generally have a light appearance when dry and a dark appearance when wet.

In one embodiment of the invention, the wetness-indicating material 24 exhibits a color intensity proportional to the degree of wetness.

In another embodiment of the invention, the wetness-indicating material 24 is disposed over a portion of the back sheet 16 in the form of patterns, shapes or letters such that said patterns, shapes or letters appear dark in contrast with a light background when the wetness-indicating material 24 becomes wet and turns dark 26. The wetness-indicating material 24 can thus be used to show patterns or designs, or to spell out words or messages which are not perceptible when the diaper is dry, but which become visually perceptible when the diaper is wet and the wetness-indicating material 24 turns dark.

In another embodiment of the invention, the article 10 comprises a liquid-permeable top sheet 14, a translucent, liquid-impermeable back sheet 16, an absorbent core 18 disposed between the top sheet 14 and the back sheet 16, and a wetness-indicating material 24 disposed within the absorbent core 18 which changes appearance when wet or in contact with any form of moisture. In this embodiment, the wetness-indicating material 24 is simply mixed in with the absorbent material 18. As the absorbent material 18 becomes wet, the wetness-indicating material 24 turns dark and is visible through the translucent back sheet 16. In this embodiment, the absorbent article 10 should tend to have a color intensity which is proportional to the total moisture content of the article. For example, the article will become wet from the interior first through to the exterior portion. As more wetness is introduced into the article, the portion of the core closest to the exterior portion changes color, making the color change more perceptible than when less moisture is in the article.

It will be understood that each of the elements described above, or two or more together, may also find a useful application in other types of applications differing from the type described above. While the invention has been illustrated and described as embodied in an absorbent article, it is not intended to be limited to the details shown, since it will be understood that various omissions, modifications, substitutions and changes in the forms and details of the formulation illustrated and in its operation can be made by those skilled in the art without departing in any way from the spirit and scope of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims:

1. An absorbent diaper comprising:

a) a liquid-permeable top sheet covering substantially all of a front side of said diaper;

b) a liquid-impermeable back sheet having an exterior-facing side and an interior-facing side covering substantially all of a back side of said diaper;

c) an absorbent core disposed between said top sheet and said back sheet;

d) a wetness-indicating material which darkens upon becoming wet forming an integral part of said diaper disposed on said back sheet in the form of patterns, shapes or letters such that said patterns, shapes or letters appear dark in contrast with a light background when said wetness-indicating material becomes wet and becomes dark; and e) said back sheet comprising a translucent moisture barrier layer on said exterior facing side and a liquid-permeable layer on said interior side, with said wetness-indicating material disposed over substantially all of said back sheet between said translucent moisture barrier layer and said liquid-permeable layer.

\* \* \* \* \*